(12) United States Patent
Haibach et al.

(10) Patent No.: US 9,901,696 B2
(45) Date of Patent: Feb. 27, 2018

(54) PATIENT INTERFACE DEVICE WITH TILT ANGLE ADJUSTING MECHANISM

(71) Applicant: KONINKLIJKE PHILIPS N.V., Eindhoven (NL)

(72) Inventors: Richard Thomas Haibach, Verona, PA (US); Derrick Blake Andrews, Markleton, PA (US)

(73) Assignee: KONINKLIJKE PHILPS N.V., Eindhoven (NL)

( * ) Notice: Subject to any disclaimer, the term of this patent is extended or adjusted under 35 U.S.C. 154(b) by 491 days.

(21) Appl. No.: 14/357,845

(22) PCT Filed: Oct. 31, 2012

(86) PCT No.: PCT/IB2012/056055
§ 371 (c)(1),
(2) Date: May 13, 2014

(87) PCT Pub. No.: WO2013/072797
PCT Pub. Date: May 23, 2013

(65) Prior Publication Data
US 2014/0326248 A1 Nov. 6, 2014

Related U.S. Application Data

(60) Provisional application No. 61/559,825, filed on Nov. 15, 2011.

(51) Int. Cl.
*A61M 16/06* (2006.01)
(52) U.S. Cl.
CPC .... *A61M 16/0622* (2014.02); *A61M 16/0605* (2014.02); *A61M 16/0666* (2013.01); *A61M 16/0683* (2013.01)

(58) Field of Classification Search
CPC .......... A61M 15/0622; A61M 16/0672; A61M 16/085; A61M 16/0683; A61M 16/0666;
(Continued)

(56) References Cited

U.S. PATENT DOCUMENTS

| 2003/0024532 A1 | 2/2003 | Snaidach |
| 2009/0044808 A1* | 2/2009 | Guney .............. A61M 16/0666 128/206.24 |

(Continued)

FOREIGN PATENT DOCUMENTS

| CN | 101282767 A | 10/2008 |
| CN | 101489617 A | 7/2009 |

(Continued)

*Primary Examiner* — (Jackie) Tan-Uyen T Ho
*Assistant Examiner* — Margaret Luarca
(74) *Attorney, Agent, or Firm* — Michael W. Haas (57) ABSTRACT

A patient interface device (8) includes a cushion assembly (16) including a nasal cushion member (20), and a frame assembly (14) having frame member (48) having a first arm (54A) and a second arm (54B). The cushion assembly is rotatably coupled to the first and second arm such that the cushion assembly rotates with respect to the frame assembly about an axis extending through the first arm and the second arm. In addition, the frame assembly includes a drive mechanism (50) received and held by the frame member, the drive mechanism being operatively coupled to the cushion assembly such that actuation of the drive mechanism changes a tilt angle of the cushion assembly relative to the frame assembly.

11 Claims, 7 Drawing Sheets

(58) Field of Classification Search
CPC .............. A61M 16/06; A61M 16/0677; A61M 16/0605; A61M 15/08
USPC ...................................... 128/206.21, 207.18
See application file for complete search history.

(56) References Cited

U.S. PATENT DOCUMENTS

| | | | | |
|---|---|---|---|---|
| 2010/0108069 A1* | 5/2010 | Chang | ................... | A61M 16/06 128/205.25 |
| 2013/0037030 A1* | 2/2013 | Matula, Jr. | ........ | A61M 16/0683 128/205.25 |
| 2014/0053852 A1* | 2/2014 | Thornton | ................ | A61F 5/566 128/862 |

FOREIGN PATENT DOCUMENTS

| | | | |
|---|---|---|---|
| CN | 101496926 | A | 8/2009 |
| CN | 101862496 | A | 10/2010 |
| CN | 101969871 | A | 2/2011 |
| EP | 1621225 | A1 | 2/2006 |
| TW | 202012496 | A | 4/2010 |
| WO | WO2004022146 | A1 | 3/2004 |
| WO | WO2006074517 | A1 | 7/2006 |
| WO | WO2007021777 | A2 | 2/2007 |
| WO | WO2008007985 | A1 | 1/2008 |
| WO | WO2009093174 | A1 | 7/2009 |
| WO | WO2010133218 | A2 | 11/2010 |
| WO | WO2010148453 | A1 | 12/2010 |
| WO | WO2011110961 | A1 | 9/2011 |

\* cited by examiner

PATIENT INTERFACE DEVICE WITH TILT ANGLE ADJUSTING MECHANISM

CROSS-REFERENCE TO RELATED APPLICATIONS

This patent application claims the priority benefit under 35 U.S.C. § 371 of international patent application no. PCT/IB2012/056055, filed Oct. 31, 2012, which claims the priority benefit under 35 U.S.C. § 119(e) of U.S. Provisional Application No. 61/559,825 filed on Nov. 15, 2011, the contents of which are herein incorporated by reference.

BACKGROUND OF THE INVENTION

1. Field of the Invention

The present invention relates to patient interface devices for communicating a gas with an airway of a user, and, in particular, to a patient interface device including a mechanism for adjusting the tilt angle (i.e., cushion to nare angle) of a nasal cushion to adjust to different patient facial geometries.

2. Description of the Related Art

There are numerous situations where it is necessary or desirable to deliver a flow of breathing gas non-invasively to the airway of a patient, i.e., without intubating the patient or surgically inserting a tracheal tube in their esophagus. For example, it is known to ventilate a patient using a technique known as non-invasive ventilation. It is also known to deliver continuous positive airway pressure (CPAP) or variable airway pressure, which varies with the patient's respiratory cycle, to treat a medical disorder, such as sleep apnea, in particular, obstructive sleep apnea (OSA).

Non-invasive ventilation and pressure support therapies involve the placement of a patient interface device including a mask component on the face of a patient. The mask component may be, without limitation, a nasal mask that covers the patient's nose, a nasal cushion having nasal prongs that are received within the patient's nares, a nasal/oral mask that covers the nose and mouth, or a full face mask that covers the patient's face. The patient interface device interfaces the ventilator or pressure support device with the airway of the patient, so that a flow of breathing gas can be delivered from the pressure/flow generating device to the airway of the patient. It is known to maintain such devices on the face of a wearer by a headgear having one or more straps adapted to fit over/around the patient's head.

For such patient interface devices, a key engineering challenge is to balance patient comfort against mask stability and mask to face seal. This is particularly true in the case of treatment of OSA, where such patient interface devices are typically worn for an extended period of time. As a patient changes sleeping positions through the course of the night, masks tend to become dislodged, and the seal can be broken. A dislodged mask can be stabilized by increasing strapping force, but increased strapping force tends to reduce patient comfort. This design conflict is further complicated by the widely varying facial geometries that a given mask design needs to accommodate. One area where facial geometries vary a great deal is the angle of the base of the nose (known as the nasolabial angle). Because this angle varies so greatly, the optimum cushion tilt varies from patient to patient. As a result, the ability to accommodate a wide range of patient nose geometries is important in terms of seal and comfort of a nasal cushion type patient interface device.

SUMMARY OF THE INVENTION

Accordingly, it is an object of the present invention to provide a patient interface device that overcomes the shortcomings of conventional patient interface devices. This object is achieved by providing a patient interface device that includes mechanism that allows the tilt angle of the associated nasal cushion to be freely and easily adjusted by the patient.

In one embodiment, a patient interface device is provided that includes a cushion assembly including a nasal cushion member, and a frame assembly having frame member having a first arm and a second arm, wherein the cushion assembly is rotatably coupled to the first arm and the second arm such that the cushion assembly is rotatable with respect to the frame assembly about an axis extending through the first arm and the second arm. In addition, the frame assembly includes a drive mechanism received and held by the frame member, the drive mechanism being operatively coupled to the cushion assembly such that actuation of the drive mechanism changes a tilt angle of the cushion assembly relative to the frame assembly.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

DETAILED DESCRIPTION OF EXEMPLARY EMBODIMENTS

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

Figure 1:
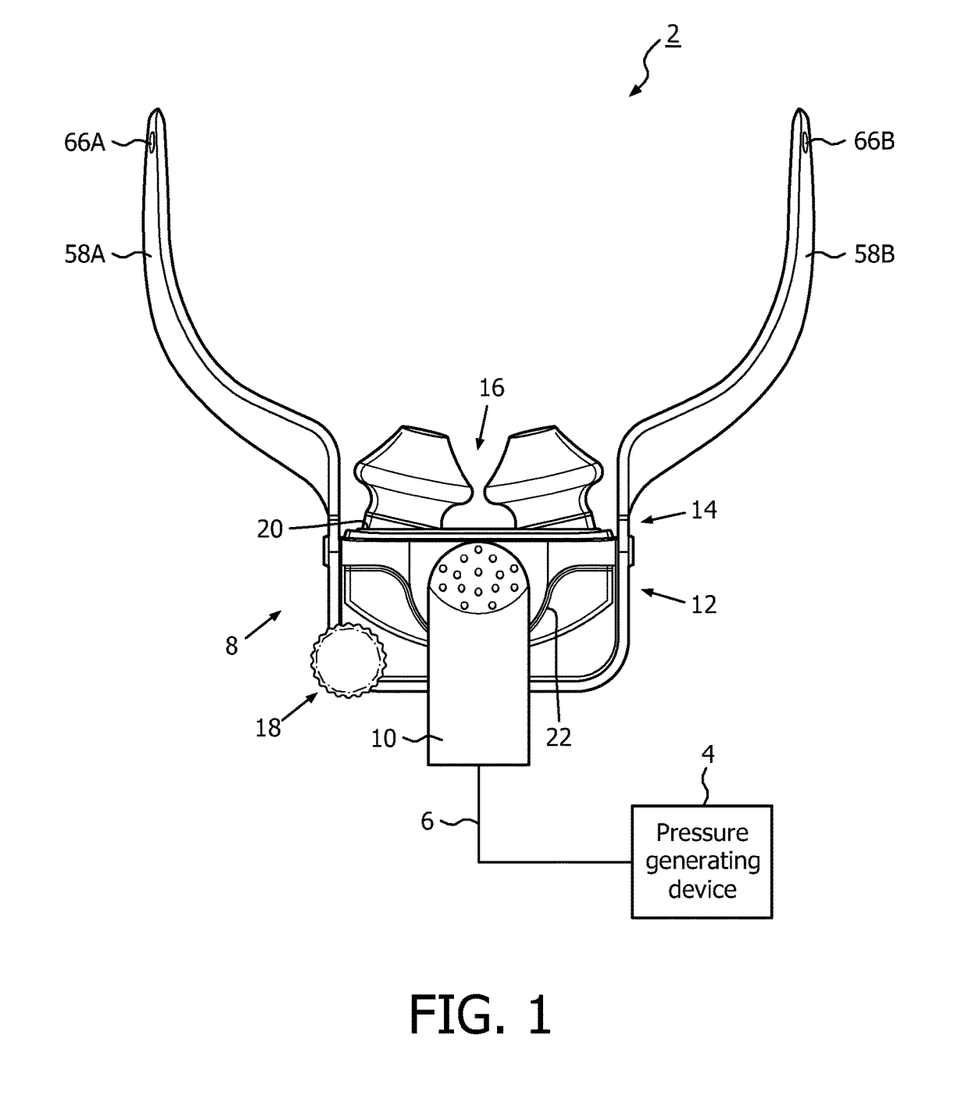
FIGS. 1 and 2 are schematic diagrams of a system adapted to provide a regimen of respiratory therapy to a patient according to one exemplary embodiment of the present invention.
Figure 2:
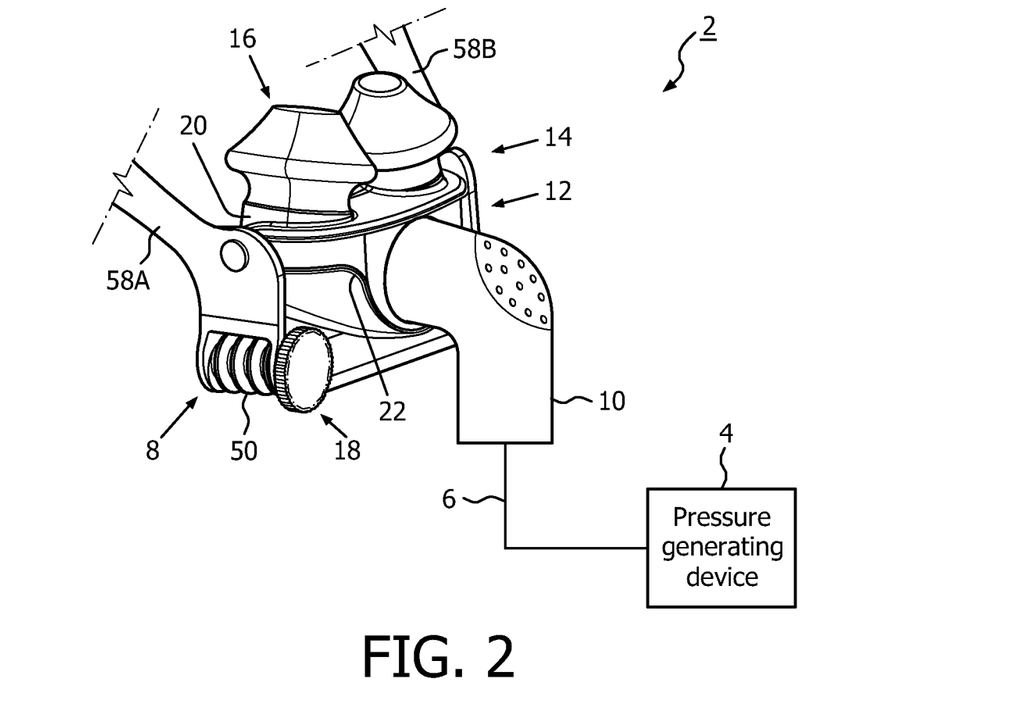

A system 2 adapted to provide a regimen of respiratory therapy to a patient according to one exemplary embodiment is generally shown in FIGS. 1 and 2. System 2 includes a pressure generating device 4, a delivery conduit 6, and a patient interface device 8 having a fluid coupling conduit 10 (patient interface device 8 is shown in front elevational view in FIG. 1 and in isometric view in FIG. 2). Pressure generating device 4 is structured to generate a flow of breathing gas and may include, without limitation, ventilators, constant pressure support devices (such as a continuous positive airway pressure device, or CPAP device), variable pressure devices (e.g., BiPAP®, Bi-Flex®, or C-Flex™ devices manufactured and distributed by Philips Respironics of Murrysville, Pa.), and auto-titration pressure support devices. Delivery conduit 6 is structured to communicate the flow of breathing gas from pressure generating device 4 to patient interface device 8 through fluid coupling conduit 10, which in the illustrated embodiment is an elbow connector. Delivery conduit 6 and patient interface device 8 are often collectively referred to as a patient circuit.

As seen in FIGS. 1 and 2, patient interface 8 includes a patient sealing assembly 12 which facilitates the delivery of the flow of breathing gas to the airway of a patient. Patient sealing assembly 12 includes a frame assembly 14 having a cushion assembly 16 rotatably coupled thereto. Patient sealing assembly 12 also includes an adjustment mechanism 18 for selectively adjusting a tilt angle of cushion assembly 16 as described in greater detail below. As also described in greater detail below, adjustment mechanism 18 is formed from components forming part of both the frame assembly 14 and the cushion assembly 16. In the exemplary embodiment, adjustment mechanism 18 is an worm gear drive mechanism. It will be appreciated, however, that adjustment mechanism 18 may comprise other types of gear drive mechanisms, such as, without limitation, a pair of spur gears with a locking mechanism or a gear and pawl type ratcheting mechanism.

Figure 3:
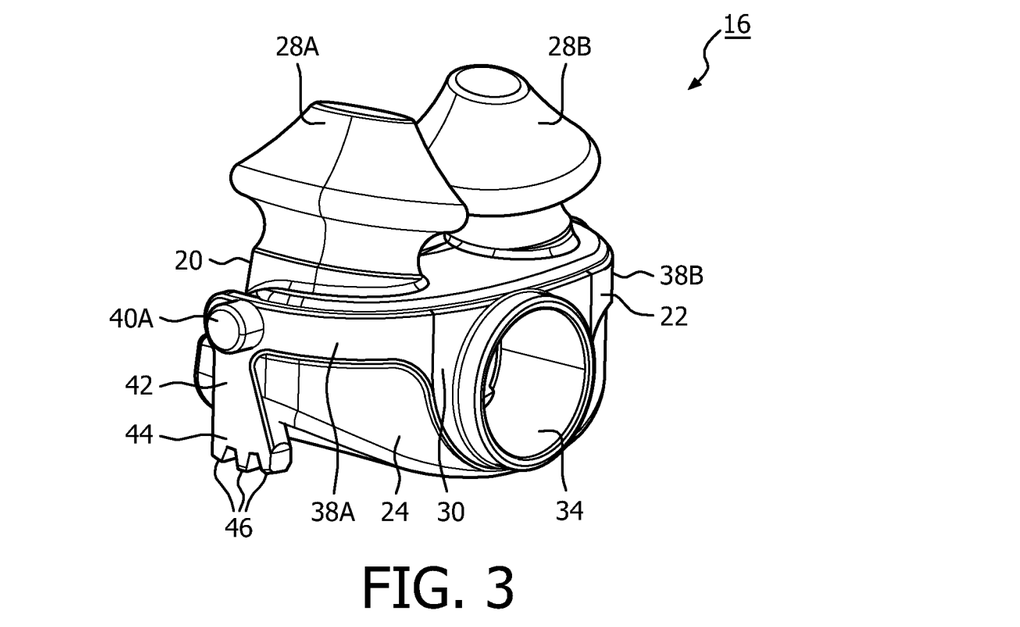
FIG. 3 is an isometric view of a cushion assembly according to the exemplary embodiment forming a part of a patient interface device of the system of FIG. 1.

FIG. 3 is an isometric view of cushion assembly 16 according to the exemplary embodiment. Cushion assembly 16 includes a nasal cushion 20 structurally and fluidly coupled to a sub-frame member 22, each of which is described below.

Figure 4:
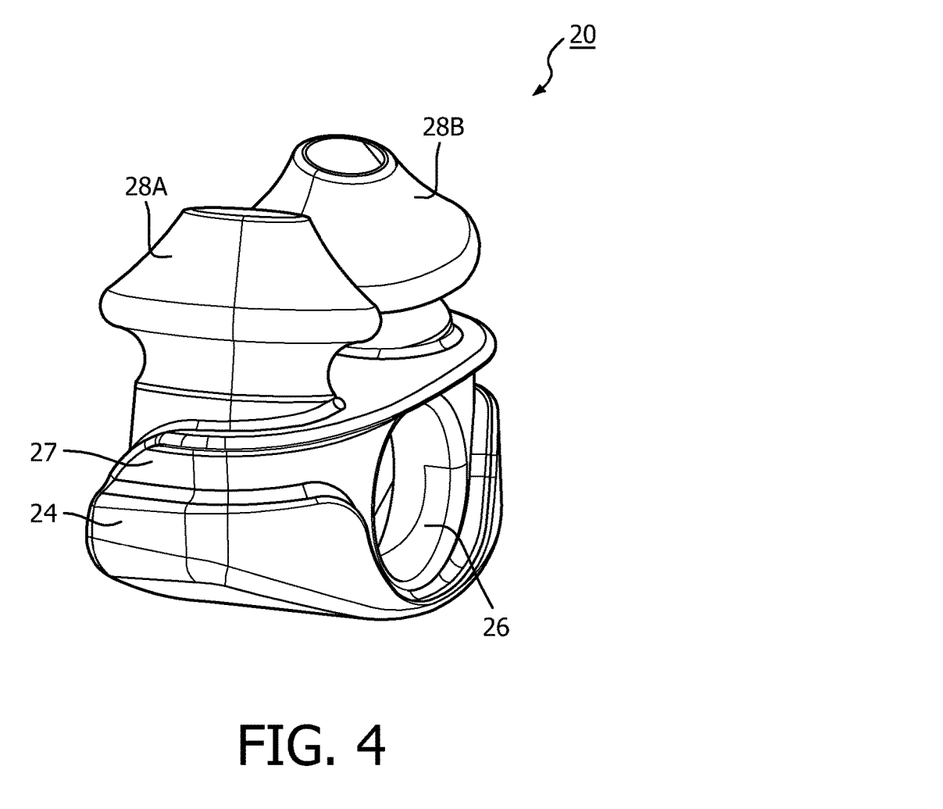
FIG. 4 is an isometric view of a nasal cushion forming a part of the cushion assembly of FIG. 3.

FIG. 4 is an isometric view of nasal cushion 20. In the illustrated embodiment, nasal cushion 20 is a "pillows" style nasal cushion made of flexible, cushiony, elastomeric material, such as, without limitation, silicone, an appropriately soft thermoplastic elastomer, a closed cell foam, or any combination of such materials. As seen in FIG. 4, the exemplary pillows style nasal cushion 20 includes a main body portion 24 having a central orifice 26, a channel 27 (shaped to receive sub-frame member 22), and nasal prongs 28A and 28B extending from a top side thereof. Alternatively, nasal cushion 20 may be a "cradle" style nasal cushion that rests beneath and covers the patient's nares, or some other suitable nasal cushion configuration structured to engage the nose of the patient.

Figure 5A:
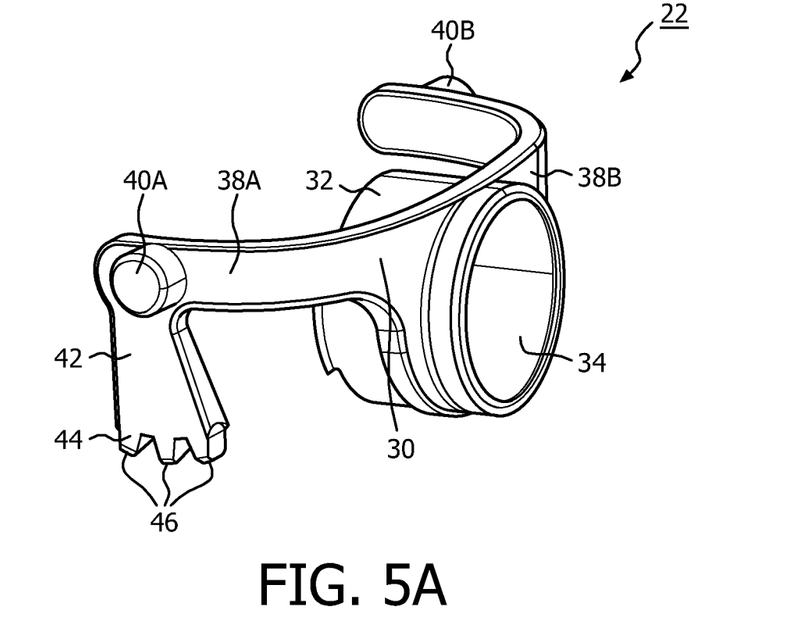
FIGS. 5A and 5B are isometric and side elevational views, respectively, of a sub-frame member forming a part of the cushion assembly of FIG. 3.
Figure 5B:
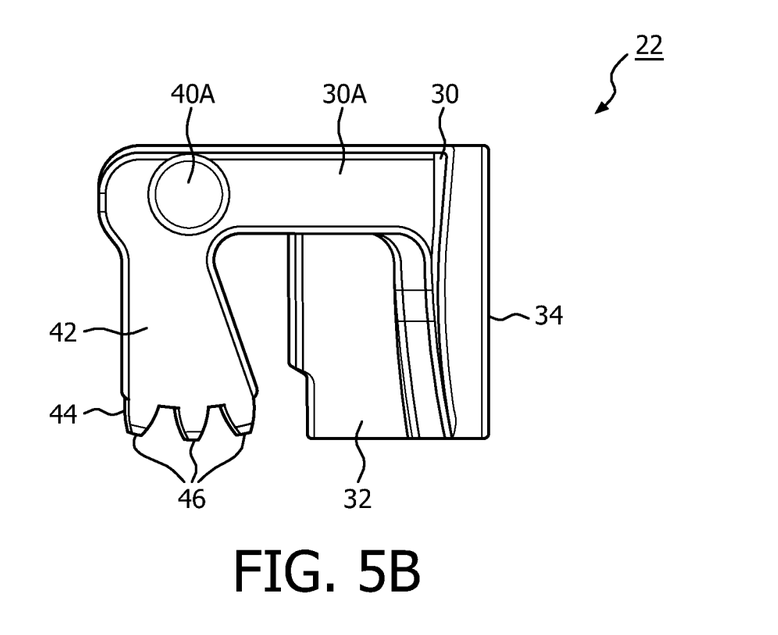

FIGS. 5A and 5B are isometric and side elevational views, respectively, of sub-frame member 22. Sub-frame member 22 is, in the exemplary embodiment, made of a rigid or semi-rigid material, such as, without limitation, an injection molded thermoplastic or silicone. Sub-frame member 22 includes a central support portion 30 having a cylindrical coupling member 32 defining a central opening 34. As seen in FIGS. 1 and 2, cylindrical coupling member 32 is structured to receive and hold fluid coupling conduit 10 through central opening 34. In addition, when cushion assembly 16 is assembled, the rear end of cylindrical coupling member 32 is received within central orifice 26 of cushion member 20, and central support portion 30 of sub-frame member 22 is received within channel 27 of cushion member 20 such that fluid coupling conduit 10 is able to be in fluid communication with the interior of nasal cushion 20 through central orifice 26. This configuration allows the flow of breathing gas from pressure generating device 4 to be communicated to nasal cushion 20, and then to the airway of a patient (through the patient's nares which are engaged by nasal prongs 28A, 28B).

In addition, referring to FIGS. 5A and 5B, central support portion 30 of sub-frame member 22 further includes arms 38A, 38B extending from opposite sides thereof. Each arm 38A, 38B includes a respective post member 40A, 40B which extends outwardly therefrom. The purpose of post members 40A, 40B is described elsewhere herein. Furthermore, sub-frame member 22 includes an extension member 42 extending downwardly from arm 38A. A distal end of extension member 42 is provided with a spur gear element 44 (also referred to as a worm gear or worm wheel) a having a plurality of teeth 46.

Figure 6:
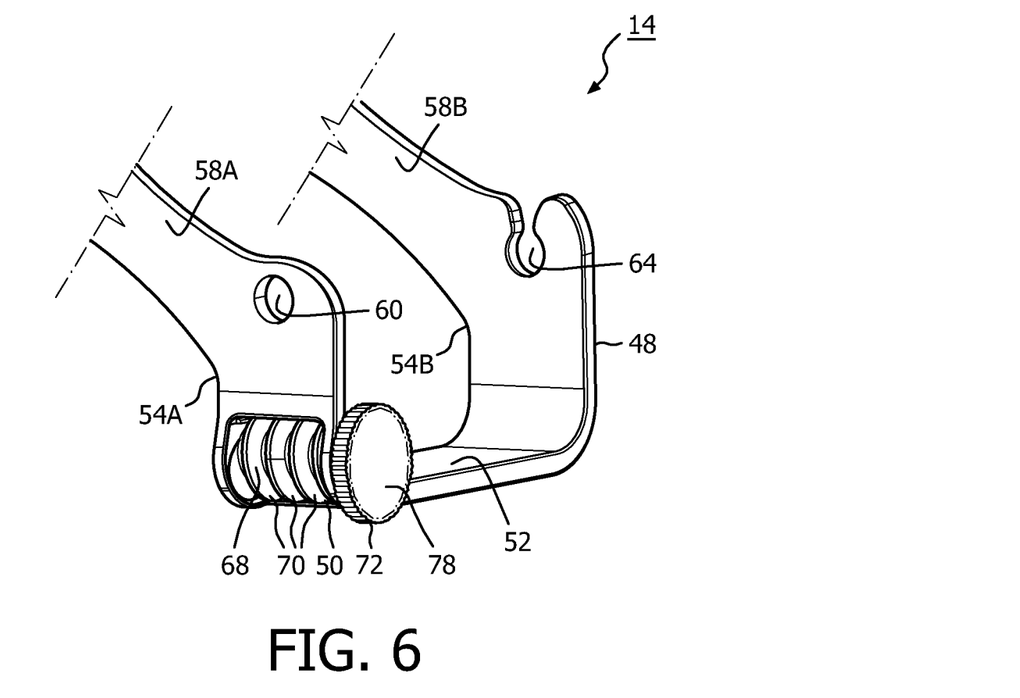
FIG. 6 is an isometric view of a frame assembly according to the exemplary embodiment forming a part of a patient interface device of the system of FIG. 1.

FIG. 6 is a partial isometric view of frame assembly 14 according to the exemplary embodiment. Frame assembly 14 includes a frame member 48 and a drive mechanism 50 received and held by frame member 48. Frame member 48 and a drive mechanism 50 are each described in detail below.

Figure 7:
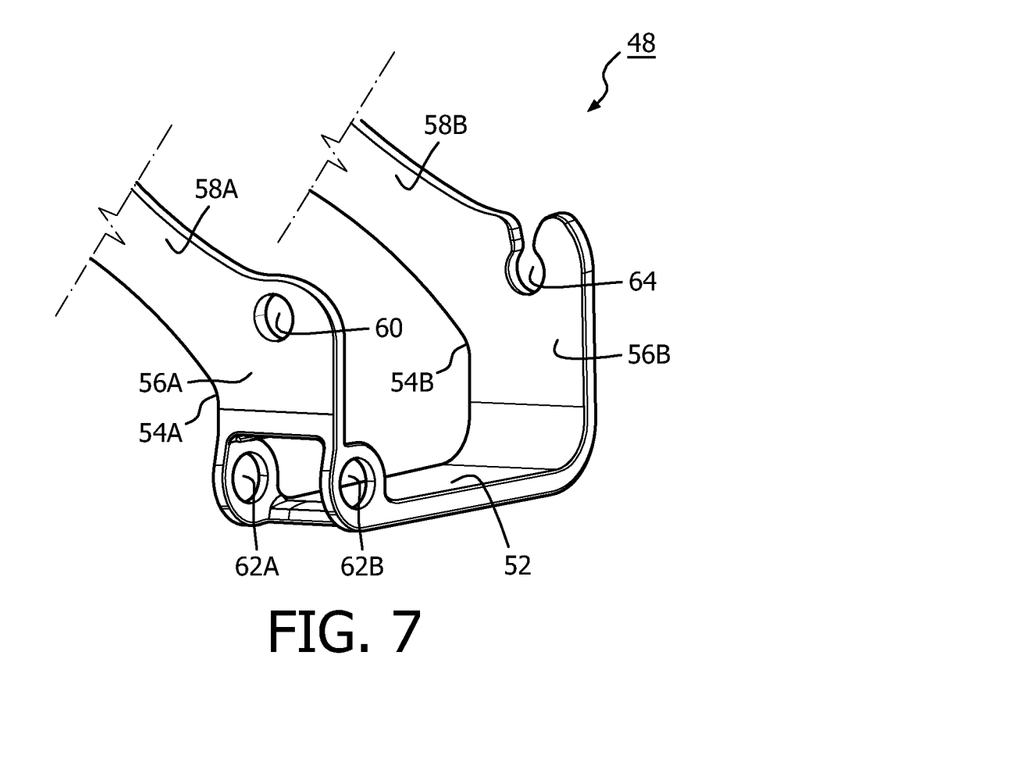
FIG. 7 is a partial isometric view of a frame member forming a part of the frame assembly of FIG. 6.

A partial isometric view of frame member 48 is provided in FIG. 7. In the illustrated embodiment, frame assembly 48 is made of a rigid or semi-rigid material, such as, without limitation, an injection molded thermoplastic or silicone. Frame member 48 includes a generally flat central portion 52 that is structured to be positioned beneath cushion assembly 16 when patient interface device 8 is assembled. Frame member 14 further includes arms 54A and 54B positioned on opposite sides of central portion 52. More specifically, arms 54A and 54B each include a respective mounting portion 56A, 56B extending in a direction that is substantially normal to the top surface of central portion 52 on either side thereof, and extension portions 58A, 58B which extend from the distal end of mounting portions 54A, 54B. In addition, as seen in FIG. 7, the distal end of mounting portion 56A includes an orifice 60 which sits in a plane that is normal to the longitudinal axis of central portion 52A. Mounting portion 56A also includes spaced concentrically aligned orifices 62A and 62B which each sits in a plane that is parallel to the longitudinal axis of central portion 52. The distal end of mounting portion 56B includes an open ended receiving slot 64 which sits in a plane that is normal to the longitudinal axis of central portion 52. In addition, as seen in FIG. 1, each extension portion 58A, 58B includes a looped connector 66A, 66B structured to enable a headgear strap (not shown) to be attached to frame member 48 in a known manner.

Figure 8:
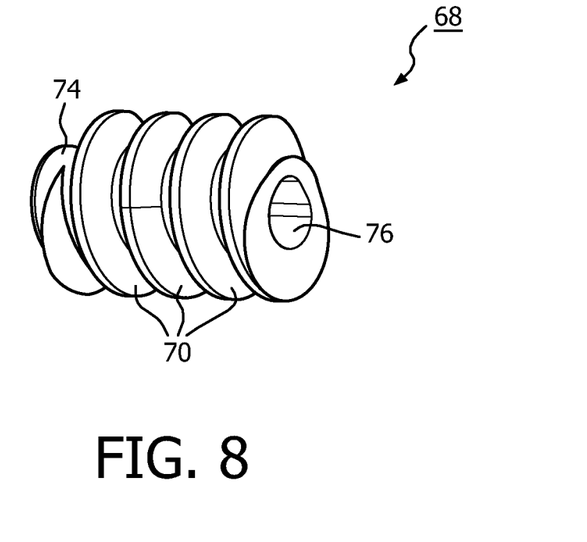
FIG. 8 is an isometric view of a screw member forming a part of the frame assembly of FIG. 6.
Figure 9:
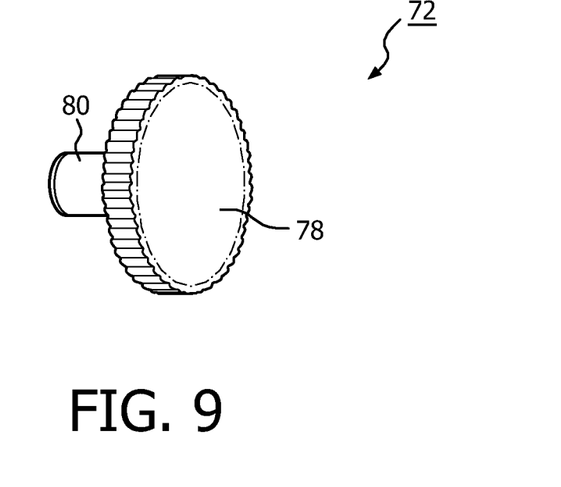
FIG. 9 is an isometric view of a knob member forming a part of the frame assembly of FIG. 6.

Referring to FIGS. 8 and 9, drive mechanism 50 includes a screw member 68 (also referred to as a worm) having a plurality of helical threads 70, and a knob member 72 that is structured to be coupled to screw member 68 in a manner such that turning of knob member 72 result in turning of screw member 68. As seen in FIG. 8, screw member 68 includes a post member 74 at a first end thereof and a hole 76 at a second end thereof. As seen in FIG. 8, knob member 72 includes a disk element 78 having a post member 80 attached thereto.

Referring to FIGS. 6-9, frame assembly 14 is assembled by inserting post member 74 of screw member 68 through orifice 62A. When this is done, hole 76 of screw member 68 will be position adjacent orifice 62B. Post member 80 of knob member 72 is then inserted into hole 76, wherein it is securely held by, for example, a friction fit. As a result, screw member 68 will be rotatably mounted to mounting portion 56A in a manner where it can be selectively rotated by turning knob member 72.

Patient interface device 8 may then be assembled by coupling cushion assembly 16 to frame assembly 14. More specifically, cushion assembly 16 is coupled to frame assembly 14 by inserting post member 40A into orifice 60 of mounting portion 56A and inserting post member 40B into slot 64 of mounting portion 56B. Is this manner, cushion assembly 16 is rotatably coupled to frame assembly 14 and is able to rotate about an axis through both orifice 60 and slot 64. In addition, when so assembled, spur gear element 44 will engage and be operatively coupled to drive mechanism 50. In particular, teeth 46 of spur gear element 44 will engage threads 70 of screw member 68. As a result, the tilt angle of cushion assembly 16 (and in particular cushion member 20) within frame assembly 14 can be selectively adjusted (to suit a particular patient's needs) by turning knob member 72, as such turning will drive screw member 68 and therefore rotate cushion assembly 16 through it interaction between screw member 68 and spur gear element 44.

Also, in the exemplary embodiment, once a desired tilt angle is obtained, cushion assembly 16 will remain fixed in place at that angle until knob member is turned again. In this manner, spur gear element 44 and drive mechanism 50 together form adjustment mechanism 18 described elsewhere herein. In the exemplary embodiment, adjustment mechanism 18 as just described is structured to resist torque applied by the weight of delivery conduit 6 and/or patent motion (for example by adding small detents to knob member 72 to engage with frame assembly 14) while still being relatively easy to actuate by the patient (e.g., by tuning knob member 72 with as little as one finger).

Figure 10:
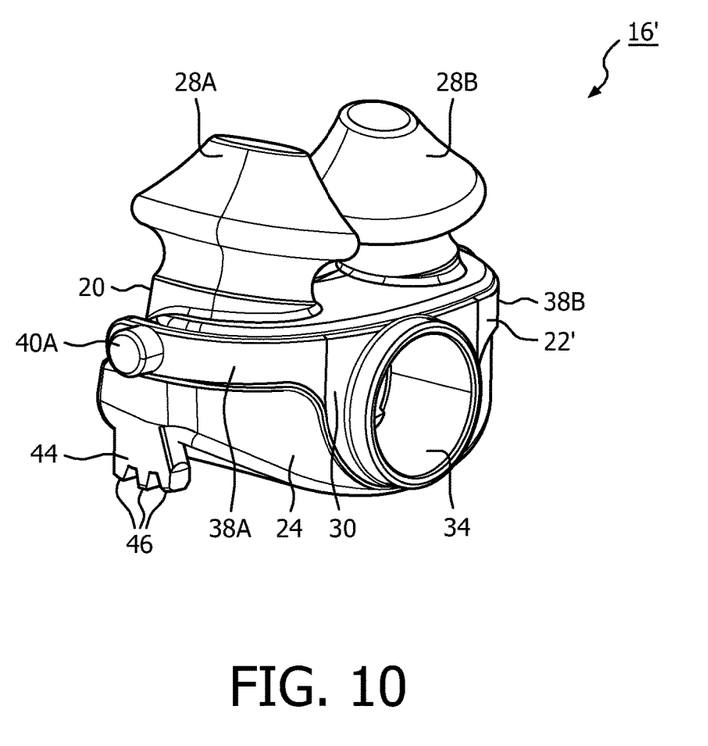
FIG. 10 is an isometric view of a cushion assembly according to an alternative exemplary embodiment that may form a part of a patient interface device of the system of FIG. 1.

FIG. 10 is an isometric view of a cushion assembly 16' according to an alternative exemplary embodiment that may be employed in patient interface device 8 in pace of cushion assembly 16. Cushion assembly 16' includes an alternative nasal cushion 20' structurally and fluidly coupled to an alternative sub-frame member 22'. Nasal cushion 20' and sub-frame member 22' include many of the same parts as nasal cushion 20 and sub-frame member 22, and like parts are labeled with like reference numerals. However, nasal cushion 20' and sub-frame member 22' differ from nasal cushion 20 and sub-frame member 22 in that spur gear element 44 is not formed as part of sub-frame member 22'. Rather, as seen in FIG. 10, spur gear element 44 is formed as an integral part of nasal cushion 20' (e.g., during the molding process). Otherwise, the cushion assembly 16' is unchanged. As a further alternative, spur gear element 44 may be formed as a separate piece (e.g., from a rigid material like plastic) that is then attached to the nasal cushion during an overmolding process.

In a further alternative exemplary embodiment, spur gear element 44 may be omitted and instead a portion of the generally soft body of nasal cushion 20 may act as a gear element. In such an embodiment, threads 70 of screw member 68 would engage (i.e., dig into) and essentially grip the portion nasal cushion 20 acting as a gear element, and rotation of screw member 68 will cause rotation of cushion assembly 16.

In addition, as described above, in the illustrated embodiment, adjustment mechanism 18 is positioned on one lateral side of frame assembly 14. In an alternative embodiment, adjustment mechanism 18 may be positioned centrally within frame assembly 14 (e.g., beneath a central portion of nasal cushion 20 and above a central portion of flat central portion 52 of frame member 48).

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A patient interface device, comprising:
a cushion assembly including a nasal cushion member, a sub-frame member and an extension member, the nasal cushion member including a central orifice and a channel surrounding the central orifice, the sub-frame member including a central support portion having a cylindrical coupling member defining a central opening, wherein a rear end of cylindrical coupling member is received within the central orifice of the nasal cushion member and the central support portion is received within the channel of the nasal cushion member;
a fluid coupling conduit coupled to the sub-frame member and in fluid communication with an interior of the nasal cushion member through the central opening and the central orifice; and a frame assembly including a frame member comprising:
   a first arm including a first mounting portion having a proximal end and a distal end,
   a second arm including a second mounting portion having a proximal end and a distal end, wherein the cushion assembly is rotatably coupled to the first arm and the second arm such that the cushion assembly is rotatable with respect to the frame assembly about an axis extending through the first arm and the second arm,
   a central portion positioned below the nasal cushion member, the central portion having a flat top surface, a first terminal end and a second terminal end opposite the first terminal end, wherein the proximal end of the first mounting portion is directly connected to the first terminal end of the central portion such that the first mounting portion extends away from the top surface of the central portion in a direction that is substantially normal to the top surface of the central portion, wherein the proximal end of the second mounting portion is directly connected to the second terminal end of the central portion such that the second mounting portion extends away from the top surface of the central portion in the direction that is substantially normal to the top surface of the central portion, and wherein the extension member extends from the cushion assembly in a direction toward the central portion, and
   a drive mechanism received and held by the frame member, the drive mechanism being operatively coupled to the extension member such that actuation of the drive mechanism changes a tilt angle of the cushion assembly relative to the frame assembly.

2. The patient interface device according to claim 1, wherein the extension member has a gear element provided on a distal end of the extension member, and wherein the drive mechanism is operatively coupled to the gear element such that actuation of the drive mechanism drives the gear element and changes the tilt angle of the cushion assembly relative to the frame assembly.

3. The patient interface device according to claim 2, wherein the cushion assembly includes a first post member extending from a first side of the cushion assembly and a second post member extending from a second side of the cushion assembly, and wherein the first post member is rotatably coupled to the first arm and the second post member is rotatably coupled to the second arm such that the cushion assembly is rotatable with respect to the frame member about an axis extending through the first post member and the second post member.

4. The patient interface device according to claim 3, wherein the first and second post members extending from opposite sides of the sub-frame member.

5. The patient interface device according to claim 4, wherein the extension member is an integral part of the sub-frame member extending downwardly from a side of the sub-frame member.

6. The patient interface device according to claim 4, wherein the sub-frame member includes a first arm having the first post member extending therefrom and a second arm having the second post member extending therefrom, and wherein the extension member extends downwardly from the first arm.

7. The patient interface device according to claim 2, wherein the gear element comprises a spur gear and the drive mechanism comprises a worm member.

8. The patient interface device according to claim 7, wherein the worm member is rotatably held by the first arm.

9. The patient interface device according to claim 8, wherein the drive mechanism further comprises a knob member coupled to the worm member, wherein the first arm includes a first orifice and a second orifice aligned with the first orifice, wherein a first end of the worm member is received through the first orifice and wherein the knob member is coupled to a second end of the worm member through the second orifice.

10. The patient interface device according to claim 2, wherein the extension member and the gear element are an integral part of the nasal cushion member.

11. The patient interface device according to claim 1, wherein the nasal cushion member includes a main body portion having first and second nasal prongs extending from a top side thereof.

* * * * *